United States Patent [19]

Siegel et al.

[11] Patent Number: 5,141,937
[45] Date of Patent: Aug. 25, 1992

[54] 7-DIPHENYLMETHYLENEBICYCLOHEPTANE OR 7-DIPHENYLMETHYLENEBICYLCOHEPTENE DERIVATIVES

[75] Inventors: Herbert Siegel, Hofheim am Taunus; Ernold Granzer, Kelkheim, both of Fed. Rep. of Germany

[73] Assignee: Hoechst Aktiengesellschaft, Frankfurt am Main, Fed. Rep. of Germany

[21] Appl. No.: 247,968

[22] Filed: Sep. 21, 1988

[30] Foreign Application Priority Data

Sep. 23, 1987 [DE] Fed. Rep. of Germany ....... 3731913

[51] Int. Cl.⁵ ............... C07D 295/192; A61K 31/535
[52] U.S. Cl. .................... 514/237.5; 514/237.8; 514/239.5; 514/255; 514/511; 514/569; 514/617; 514/619; 514/622; 514/640; 514/648; 514/676; 514/681; 514/717; 514/719; 514/724; 544/165; 544/174; 544/176; 544/178; 544/391; 544/396; 564/163; 564/172; 564/180; 564/315; 564/265
[58] Field of Search ............... 564/253, 259, 316, 163, 564/172, 180, 265, 315; 548/427; 568/425; 514/255, 238.8, 239.5, 585, 237.5, 237.8, 534, 553, 724, 511, 569, 617, 619, 622, 640, 648, 676, 681, 717, 719, 729; 544/162, 391, 165, 174, 176, 178, 391, 396

[56] References Cited

U.S. PATENT DOCUMENTS 4,550,186 10/1985 McPhail et al. .................... 514/499
4,647,575 3/1987 Siegel et al. ........................ 514/396

OTHER PUBLICATIONS

Yates, P. & Kronis, J., "Aliphatic diazo compounds. XIV. The synthesis of 7-substituted 3-diazo-2-norbornanones", Dec. 14, 1983, Can. J. Chem., vol. 62, 1984.
Synthesis, International Journal of Methods in Synthetic Organic Chemistry, No. 8, Aug. 1985, pp. 798-801.
Annalen der Chemie, 566, 27 (1950) (including pages 27-59).
J. Med. Pharm. Chem., vol. 5, No. 5 (1962), pp. 883-896.

*Primary Examiner*—Mukund J. Shah
*Assistant Examiner*—Jyothsna Venkat
*Attorney, Agent, or Firm*—Finnegan, Henderson, Farabow, Garrett and Dunner

[57] ABSTRACT

Pharmaceutical products containing a 7-diphenylmethylenebicycloheptane or 7-diphenylmethylenebicycloheptene derivative of the formula I

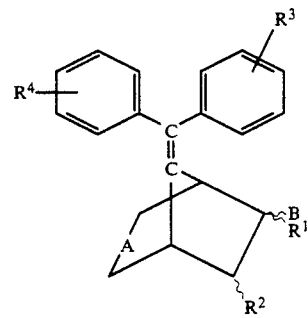

in which A, B, $R^1$, $R^2$, $R^3$ and $R^4$ have the stated meanings, or a physiologically tolerated acid addition salt of these compounds, and the use thereof as hypolipidemics are described. In addition, new 7-diphenylmethylenebicycloheptane and -heptene derivatives of the formula Ia

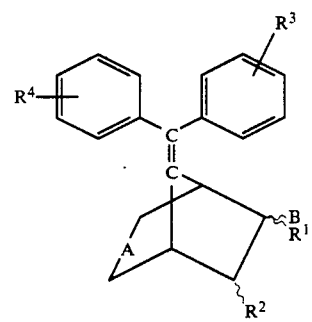

in which A, B, $R^1$, $R^2$, $R^3$ and $R^4$ have the stated meanings, and the physiologically tolerated acid addition salts thereof, as well as processes for the preparation thereof, are described.

7 Claims, No Drawings

7-DIPHENYLMETHYLENEBICYCLOHEPTANE OR 7-DIPHENYLMETHYLENEBICYLCOHEPTENE DERIVATIVES

The invention relates to pharmaceutical products which contain 7-diphenylmethylenebicycloheptanes and -enes, and the use of these compounds as medicaments, especially for the treatment of hyperlipidemias. The invention also relates to new 7-diphenylmethylenebicycloheptanes and 7-diphenylmethylenebicycloheptenes and a process for the preparation thereof.

There has already been a description of the hypolipidemic action of 7-diphenylmethylenebicycloheptanes and -heptenes which are bonded in the 2 position, directly or via a chain of carbon atoms, to an imidazole residue on the nitrogen. German Patent Application DE-A 3,410,498.4 (corresponds to EP-A 0,158,144 and U.S. Pat. No. 4,647,575) relates to these compounds.

It has now been found, surprisingly, that 7-diphenylmethylenebicycloheptane and -heptene derivatives which are not imidazole-substituted likewise have a very strong hypolipidemic action. The active compounds take the form of 7-diphenylmethylenebicycloheptanes and -heptenes which are substituted in the 2 position by oxygen- or nitrogen-containing functional groups.

Hence the invention relates to pharmaceutical products containing a 7-diphenylmethylenebicycloheptane or -heptene of the general formula I

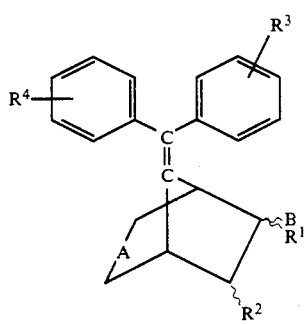

in which
A is a single or double bond,
B is a carboxamide group of the formula

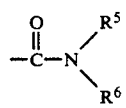

or a methyleneamino group of the formula

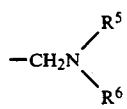

in which $R^5$ and $R^6$ are identical or different and denote hydrogen or $C_1$-$C_4$-alkyl, or in which $R^5$ and $R^6$ form, together with the nitrogen atom, a morpholine or piperazine ring, or a piperazine ring which is substituted in the 4-position by $C_1$-$C_4$-alkyl, or B is —OH, —CN, —$CO_2H$, —$CO_2$-($C_1$-$C_4$)-alkyl or

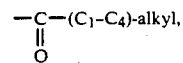

$R^1$ is hydrogen, chlorine, $C_1$-$C_4$-alkyl or, together with B, is an oxime group (=N—OH) or oxygen bonded by a double bond (=O),
$R^2$ is hydrogen or, together with B, is a dicarboxylic anhydride

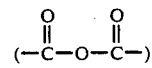

or a dicarboximide

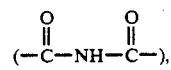

$R^3$ and $R^4$ are identical or different and denote hydrogen, halogen, ($C_1$-$C_4$)-alkyl, ($C_1$-$C_4$)-alkoxy, trifluoromethyl, hydroxyl, amino, ($C_1$-$C_4$)-alkylamino or di-($C_1$-$C_4$)-alkylamino,
or, in the case of basic substituents for B the physiologically tolerated acid addition salts thereof.

The invention also relates to the use of the compounds of the formula I as medicaments, in particular as hypolipidemics, and the use for the preparation of medicaments.

The wavy lines in formula I and in the formula which follow indicate that the substituents can be located both in the endo and in the exo position on the bicyclic moiety.

The alkyl and alkoxy radicals are straight-chain or branched.

Preferred as active substances are compounds of the formula I in which
A denotes a single bond,
B denotes a —$CO_2H$, —CH, —$CH_2OH$ or —OH group,
$R^1$ denotes hydrogen or, together with B, denotes oxygen which is bonded via a double bond (=O), or the oxime group (=N—OH),
$R^2$ denotes hydrogen, and
$R^3$ and $R^4$ denote hydrogen or halogen.

Some of the compounds of the formula I are new. Hence the invention also relates to new 7-diphenylmethylene-bicycloheptanes and 7-diphenylmethylenebicycloheptenes of the formula Ia

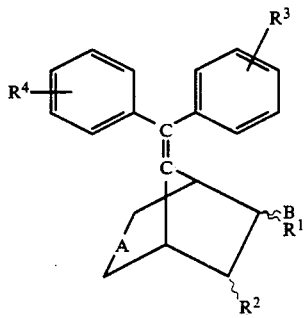

in which
A is a single or double bond,
B is a carboxamide group of the formula

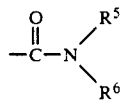

or a methyleneamino group of the formula

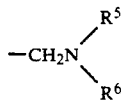

in which $R^5$ and $R^6$ are identical or different and denote hydrogen or $C_1$-$C_4$-alkyl, or in which $R^5$ and $R^6$ form, together with the nitrogen atom, a morpholine or piperazine ring, or a piperazine ring which is substituted in the 4 position by $C_1$-$C_4$-alkyl, $R^1$ is hydrogen or chlorine or, together with B, is an oxime group (=N—OH), $R^2$ represents hydrogen, and $R^3$ and $R^4$ are identical or different and denote hydrogen, halogen, ($C_1$-$C_4$)-alkyl, ($C_1$-$C_4$)-alkoxy, trifluoromethyl, hydroxyl, amino, ($C_1$-$C_4$)-alkylamino or di-($C_1$-$C_4$)-alkylamino, and to the physiologically tolerated acid addition salts thereof.

Compounds of the formula Ia in which A is a single bond, B and $R^1$ together form the oxime group, and $R^3$ and $R^4$ denote hydrogen or chlorine are preferred.

The invention also relates to processes for the preparation of compounds of the formula Ia, which comprise A) converting a bicycloheptane- or bicycloheptenecarboxylic acid of the formula Ib

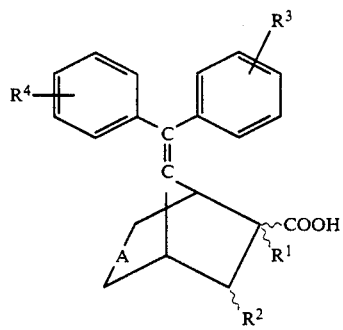

with a chlorinating agent into the corresponding acid chloride, and then reacting with an amine

to give a compound of the formula Ia in which A, $R^2$, $R^3$ and $R^4$ have the indicated meanings, $R^1$ is hydrogen or chlorine, and B represents the

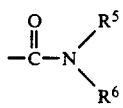

group, and, where appropriate, reducing a resulting carboxamide derivative to a compound of the formula Ia in which A, $R^2$, $R^3$ and $R^4$ have the indicated meanings, $R^1$ is hydrogen or chlorine, and B represents the

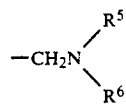

group, or

B) reacting a ketone of the formula Ic

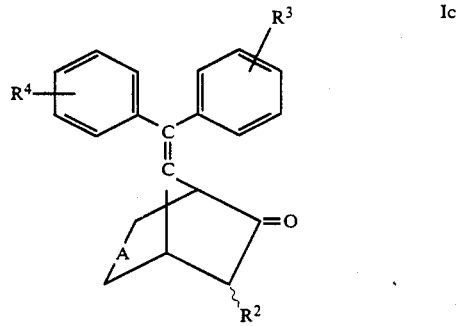

with hydroxylamine hydrochloride to give a compound of the formula Ia in which A, $R^2$, $R^3$ and $R^4$ have the indicated meaning, and $R^1$ and B together form the =NOH group, and, where appropriate, hydrogenating the double bond in a resulting compound of the formula Ia in which A represents a double bond and, where appropriate, converting a compound of the formula Ia into a physiologically tolerated acid addition salt.

The compounds of the formula Ib are either described in the literature (cf., for example, Synthesis 1985, 798 and Ann. 566, pages 27 et seq. (1950)) or prepared in analogy to the methods described therein.

Examples of suitable chlorinating agents are thionyl chloride or phosgene.

Where A represents a double bond, this can be hydrogenated by methods known per se, for example with 5% platinum on charcoal. It is expedient in the preparation of compounds of the formula Ia by process A to hydrogenate the bicycloheptenecarboxylic acid to give the bicycloheptanecarboxylic acid. The resulting bicycloheptanecarboxylic acid is then converted in a manner known per se, for example in a one-pot reaction with thionyl chloride, into the corresponding acid chloride, and the latter is then reacted with amine to give the carboxamide.

The reduction of the carboxamides obtained by process A is expediently carried out with lithium aluminum hydride in an aprotic solvent such as tetrahydrofuran.

The ketones of the formula Ic which are employed as starting compounds in process B either are described in the literature (cf. for example, Synthesis 1985, 798 and EP-A 0,158,144) or can be prepared in analogy to the described methods.

The reaction with hydroxylamine hydrochloride is preferably carried out in the presence of potassium carbonate in ethanol as solvent.

It is possible to prepare acid addition salts from the amines of the general formula Ia. suitable for this purpose are all acids which form physiologically tolerated salts. These include both inorganic acids such as, for example, hydrochloric acid, nitric acid and sulfuric acid, and mono- and bifunctional organic acids, especially carboxylic acids such as acetic acid, succinic acid, tartaric acid etc.

Those compounds of the formula I not covered by formula Ia are described in the literature (cf., for example, EP-A 0,158,144, Synthesis 1985, 798, Ann 566 27 et seq. (1950) and J. Med. Phar. Chem. 5, 883 (1962)) or can be prepared in analogy to the described methods.

The compounds of the formula I have valuable pharmacological properties, in particular they exhibit a very strong and beneficial effect on serum lipoproteins. Hence the invention relates to pharmaceutical products based on these compounds, and to the use thereof, in particular for affecting serum lipoproteins.

It is generally recognized that hyperlipoproteinemias represent a considerable risk factor for the development of arteriosclerotic vascular lesions, especially of coronary heart disease. Hence, it is extremely important to lower elevated serum lipoproteins for the prophylaxis and regression of arteriosclerotic lesions. However, very particular classes of serum lipoproteins are important in this, because the low density (LDL) and very low density (VLDL) lipoproteins represent an atherogenic risk factor whereas the high density lipoproteins (HDL) function as protectives against arteriosclerotic vascular lesions. Accordingly, hypolipidemics ought to lower VLDL-cholesterol and LDL-cholesterol in the serum while, where possible, leaving unaffected the HDL-chloresterol concentration, so that the antiatherogenic index $$\frac{HDL - C}{LDL - C}$$

does not fall below 1 by comparison with normal controls.

the compounds of the formula I have valuable therapeutic properties. Thus, they lower, in particular, the concentration of LDL and VLDL but lower the HDL fraction only in excessive dosage which is sufficient to reduce the LDL-cholesterol concentrations by more than about 50%, so that the result is a great reduction in the LDL fraction without affecting the HDL fraction in the therapeutically utilizable range. Hence these compounds represent a considerable advance from the comparison compound clofibrate which, besides LDL, always brings about a very great reduction in HDL, as is evident from the data described hereinafter Hence the compounds of the formula I can be used for the prophylaxis and regression of arteriosclerotic lesions, in that they eliminate a casual risk factor. These include not only primary hyperlipidemias but also certain secondary hyperlipidemias such as occur, for example, with diabetes. The action of the listed compounds on the serum lipoproteins was investigated in male Wistar rats which were treated by gavage for 7 days with the listed compounds suspended in polyethylene glycol 400. The study included a control group which received only the solvent polyethylene glycol 400, and, in most experiments, a group of rats with the standard hypolipidemic clofibrate in the dose 100 mg/kg/day; this is the minimum active dose in male rats. As a rule, 10 animals were employed in each group and, at the end of the treatment, blood was taken from their orbital plexus under light ether anesthesia. The serum lipoproteins from the rat serum obtained were separated into the following density classes in a preparative ultracentrifuge: VLDL<1.006; LDL 1.006 to 1.04; HDL 1.04 to 1.21.

Since, in contrast to humans, the serum lipoproteins of rats contain about 4/5 HDL-chloresterol and only 1/5 LDL-cholesterol and only very small amounts of VLDL (conversely about 4/5 LDL and VLDL and only 1/5 HDL in humans), a prerequisite for assessment of a hypolipidemic action in rats is fractionation of the rat serum into Lipoprotein classes. This is because simply lowering the total serum cholesterol content in rats would indicate only the undesired lowering of the antiatherogenic HDL class which predominates in rats. A desired lowering of LDL with, at the same time, a desired increase in HDL would, however, have no (considerable) effect on the total cholesterol content in rat serum.

The cholesterol contained in the lipoprotein fractions isolated in the ultracentrifuge was determined completely enzymatically by the CHOD-PAP method using the Boehringer-Mannheim assay kit, and the values were converted into $\mu g/ml$ of serum. The percentage change of the lipoprotein cholesterol in the treated group compared with a control group included in the study under identical conditions is indicated in Table I which is included. It is evident from Table I that clofibrate reduces the HDL and LDL fractions to similar extents, so that the antiatherogenic index remains 1, whereas the compounds of the formula I exert a highly selective lowering action on the atherogenic lipoprotein fractions (VLDL and LDL), and leave the protective HDL fraction (as long as there is no overdosage) essentially unaffected. The investigated compounds additionally have a considerably higher efficacy than clofibrate, which, in the case of the particularly highly active compound of Example 22, is $10^{+5}$ times greater than clofibrate. The compound of Example 22 is, moreover, distinguished by another advantage deriving from the ratio between its minimum dose for hypolipidemic activity and that for a uterotrophic action: it is $\geq 30$.

For the other compounds listed, the minimum dose for hypolipidemic activity is of approximately the same order of magnitude as that for the uterotrophic action.

TABLE I

Percent changes in the lipoproteins in rat serum after oral administration of the compounds for 7 days

| of Example No. | Dosage mg/kg/day | Percent change in cholesterol (relative to the control groups) in the serum lipoprotein fractions | | | $\frac{HDL - C}{LDL - C}$ | Minimum dose for activity mg/kg/day | Uterotrophic action mg/kg/day |
|---|---|---|---|---|---|---|---|
| | | VLDL | LDL | HDL | | | |
| 22 | 0.1 | −47 | −97 | −92 | | | |
| | 0.01 | −20 | −34 | −8 | 1.38 | 0.01 | $\geq 0.3$ |
| 21 | 0.1 | −34 | −43 | −22 | 1.38 | | |
| | 0.03 | +5 | −83 | −47 | 3.11 | 0.03 | $\geq 0.01$ |
| 19 | 0.3 | +3 | −81 | −28 | 3.73 | | |
| | 0.1 | −18 | −84 | −85 | 0.94 | 0.1 | 0.1 |

TABLE I-continued

Percent changes in the lipoproteins in rat serum after oral administration of the compounds for 7 days

| of Example No. | Dosage mg/kg/day | Percent change in cholesterol (relative to the control groups) in the serum lipoprotein fractions | | | $\frac{HDL - C}{LDL - C}$ | Minimum dose for activity mg/kg/day | Uterotrophic action mg/kg/day |
| --- | --- | --- | --- | --- | --- | --- | --- |
| | | VLDL | LDL | HDL | | | |
| 9 | 30 | | −90 | −93 | | | |
| | 3 | | −85 | −84 | | 0.3 | |
| | 0.3 | −10 | −66 | −27 | 2.13 | | |
| 14 | 3 | −88 | −98 | −97 | | | |
| | 0.3 | −59 | −95 | −96 | 0.77 | 0.3 | 0.3 |
| 20 | 3 | −26 | −77 | −91 | | 0.3 | 0.3 |
| | 0.3 | −15 | −66 | −17 | 2.43 | | |
| 1 | 1 | −6 | −49 | −22 | | 0.3 | 0.3 |
| | 0.3 | +12 | −34 | −17 | 1.27 | | |
| 18 | 3 | −38 | −93 | −95 | | 0.3 | 0.3 |
| | 0.3 | +5 | −21 | −21 | 1.01 | | |
| 13 | 3 | −30 | −63 | −35 | | 0.3−1 | |
| | 0.3 | −12 | −12 | −7 | 1.05 | | |
| 11 | 3 | −26 | −36 | −22 | 1.22 | 1−3 | |
| 5 | 3 | −52 | −53 | −5 | 2.0 | 3 | |
| 15 | 3 | −50 | −93 | −96 | 0.65 | 3 | 3 |
| 17 | 3 | −41 | −92 | −59 | 5.05 | 3 | |
| 3 | 3 | −28 | −33 | +4 | 1.55 | 3 | |
| 7 | 3 | −8 | −20 | +3 | 1.29 | 3 | |
| 12 | 3 | −51 | −33 | −5 | 1.42 | 3 | |
| Clofibrate (comparison substance) | 100 | −32 | −35 | −32 | 1.04 | 100 | none |

Particularly suitable therapeutic formulations of the compounds of the formula I are tablets, coated tablets, capsules, suppositories and syrups. In this connection, the new compounds can be used either alone or mixed with pharmacologically acceptable vehicles. A form for oral use is preferred. For this purpose, the active compounds are preferably mixed with auxiliaries known per se and converted by methods known per se into suitable dosage forms, such as tablets, hard gelatin capsules, aqueous or oily suspensions or aqueous or oily solutions. Examples of inert vehicles which can be used are magnesium carbonate, lactose or corn starch, with the addition of other substances such as, for example, magnesium stearate. In this connection, the formulation can be carried out as dry or wet granules. Particularly suitable oily vehicles or solvents are vegetable and animal oils such as, for example, sunflower oil or fish liver oil. A suitable daily dose is about 1 mg to 200 mg, preferably 2 mg to 20 mg, and when the compound of Example 22 is used, 0.5–5 mg, preferably 0.8–2 mg. A dosage unit preferably contains 0.5 to 2 mg of active substance of Example 22.

In the treatment of disturbances of lipid metabolism, the formulations can, apart from the customary fillers and vehicles, also contain an antihypertensive such as, for example, a saluretic, reserpine, hydralazine, guanethidine, α-methyldopa, clonidine, ACE inhibitor or a β-sympatholytic, a compound having antithrombotic activity, such as, for example, acetylsalicylic acid, sulfinpyrazone, triclopidine and heparinoids, or an agent having antihyperuricemic activity, and oral antidiabetic, a geriatric agent or an agent acting to increase blood flow.

The examples which follow explain the invention.

EXAMPLE 1

7-diphenylmethylenebicyclo[2.2.1]heptane-2-one oxime 33.7 g (129 mmol) of 7-diphenylmethylenebicyclo[2.2.1]-heptane-2-one were stirred with 9.9 g (142 mmol) of hydroxylamine hydrochloride and 17.8 g (129 mmol) of potassium carbonate in 50 ml of ethanol at room temperature for four hours. Then 200 ml of water were added, and the mixture was extracted three times wit 100 ml of methylene chloride. The combined methylene chloride phases were washed three times with 300 ml of water, dried over sodium sulfate and concentrated in vacuo. 31.7 g of 7-diphenylmethylenebicyclo[2.2.1-]heptane-2-one oxime were obtained as an amorphous solid.

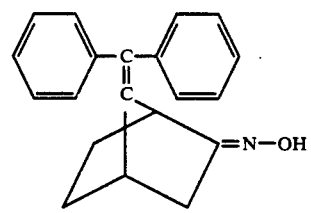

NMR (CDCl$_3$): 1.4–2.8 (m, 9H); 2.9–3.1 (m, 1H); 3.3–3.5 (m, 1H); 7.0–7.5 (m, 10H); 7.85 (s, —OH)
Anal.: C$_{20}$H$_{19}$NO: 289.38 calc.: C 83.01, H 6.62, N 4.84, found: C 82.6, H 6.8, N 4.5,

EXAMPLE 2

Dimethylamide of endo-7-(4,4'-dichlorodiphenylmethylene)-bicyclo[2.2.1-]heptane-2-carboxylic acid a)
Endo-7-(4,4'-dichlorodiphenylmethylene)bicyclo[2.2.1]-hept-5-ene-2-carboxylic acid 35 g (117 mmol) of 4,4'-dichlorodiphenylfulvene and 16.8 g (234 mmol) of acrylic acid were left to react together at room temperature for two weeks. The resulting solid mass were then recrystallized from 220 ml of ethyl acetate. 21.8 g of the endo adduct were obtained as white crystals of melting point 182° C.

b)
Endo-7-(4,4'-dichlorodiphenylmethylene)bicyclo[2.2.1]-heptane-2-carboxylic acid 21.7 g (58.5 mmol) of the carboxylic acid obtained under a) were dissolved in 150 ml of tetrahydrofuran. 1 g of Pd/C was added, the mixture was then hydrogenated at room temperature under atmospheric pressure until one equivalent of hydrogen had been absorbed. The catalyst was filtered off with suction, and the solvent was removed by distillation in a rotary evaporator, leaving 22.1 g of the hydrogenated acid as white crystals of melting point 238° C.

c)
Dimethylamide of endo-7-(4,4'-dichlorodiphenylmethylene) bicyclo[2.2.1]heptane-2-carboxylic acid 22.0 g (59 mmol) of the carboxylic acid obtained under b) were dissolved in 200 ml of toluene. Two drops of pyridine were added as catalyst and then 11.3 g (95 mmol) of thionyl chloride were added dropwise, and the mixture was refluxed for three hours. The solvent and excess thionyl chloride were then removed by distillation, and the residue was dissolved in 200 ml of tetrahydrofuran. Subsequently, at 0° C. 9.0 g (200 mmol) of dimethylamine were added to the solution of the acid chloride, and the mixture was stirred overnight. The reaction mixture was worked up in analogy to Example 1) using methylene chloride/water. 19.2 g of the dimethylamide of endo-7-(4,4'-dichlorodiphenylmethyl-methylene) bicyclo[2.2.1]heptane-2-carboxylic acid were obtained as a yellowish oil.

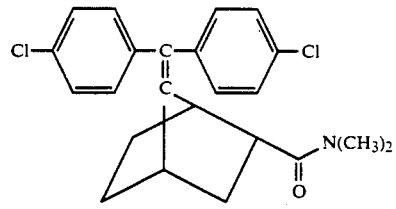

NMR (CDCl$_3$): 1.5–3.5 (m, 9H); 2.9 (s, 2CH$_3$); 6.8–7.4 (dq, 8H).

EXAMPLE 3

Endo-2-dimethylaminomethyl-7-(4,4'-dichlorodiphenylmethylene) bicyclo[2.2.1]heptane hydrochloride 0.6 g (17.3 mmol) of lithium aluminum hydride were introduced into 20 ml of diethyl ether. 9.2 g (23 mmol) of the dimethylamide of endo-7-(4,4'-dichlorodiphenylmethylene) bicyclo[2.2.1]heptane-2-carboxylic acid in 50 ml of diethyl ether were added dropwise to this suspension. The mixture was refluxed for eight hours, left to cool and, at 0° C., dilute hydrochloric acid was slowly added until the pH had reached 7. 100 ml of water were added, and the ether phase was separated off. The aqueous phase was extracted twice more with 50 ml of methylene choride. The ether phase was combined with the methylene chloride phases, and the mixture was washed twice with 200 ml of water and dried over sodium sulfate. The drying agent was filtered off and the solvent was removed, leaving 8.8 g of reaction product as an oil. The oil was dissolved in 100 ml of diethyl ether, and hydrogen chloride was used to precipitate the hydrochloride of the amine obtained in the reduction. 5.0 g of white crystals of melting point 216° C. were obtained.

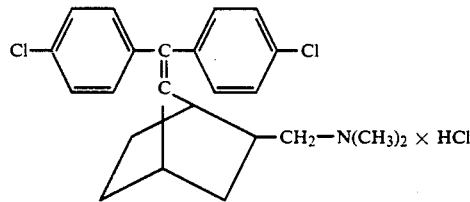

NMR (DMSO): 1.0–3.5 (m, 11H); 2.7 (s, 2CH$_3$); 6.8–7.5 (dq, 8H).

Anal.: C$_{24}$H$_{26}$Cl$_3$N: 434.85 calc.: C 66.29, H 6.03, N 3.22, Cl 24.46 found: C 65.1, H 5.9, N 3.1, Cl 24.2

The following new compounds were prepared in an analogous manner:

| Example | A | B | R$^1$ | R$^2$ | R$^3$ | R$^4$ | config. | phys. data |
|---------|---|---|-------|-------|-------|-------|---------|------------|
| 4 | — | −C(=O)−N⟨O⟩ (morpholine amide) | H | H | Cl | H | endo | NMR: 1.4–3.2(m, 11H), 3.2–4.0 (m, 6H); 6.8–7.6 (m, 9H) |
| 5 | — | −CH$_2$−N⟨O⟩ (morpholinomethyl) | H | H | Cl | H | endo | HCl salt: MP = 240° C. |

-continued

| Example | A | B | $R^1$ | $R^2$ | $R^3$ | $R^4$ | config. | phys. data |
|---|---|---|---|---|---|---|---|---|
| 6 | — | —C(=O)—N(piperazine)N—CH₃ | | H | H | Cl | Cl | endo | NMR: 1.5–4.0(m, 17H), 2.25(s, CH₃), 6.8–7.5(dq, 8H) |
| 7 | — | —CH₂—N(piperazine)N—CH₃ | | H | H | Cl | Cl | endo | HCl salt: MP = 210° C. |
| 8 | — | B + $R^1$ = NOH | | | H | Cl | Cl | — | NMR: 1.5–3.5(m, 8H), 6.8–7.5(dq, 8H). | prepared by described processes

| Example | A | B | $R^2$ | $R^1$ | $R^3$ | $R^4$ | config. | reference |
|---|---|---|---|---|---|---|---|---|
| 9 | — | —CN | H | H | H | H | endo | Ann. 566, 27 |
| 10 | = | $R^2$, B = —C(=O)—O—C(=O)— | | H | H | H | endo | " " |
| 11 | — | $R^2$, B = —C(=O)—N(H)—C(=O)— | | H | H | H | endo | J. Med. Pharm. Chem. 5, 883 (1962) |
| 12 | = | —CN | H | H | H | H | exo | Synth. 1985, 798 |
| 13 | = | —CN | H | H | H | H | endo | " |
| 14 | = | —CO₂H | H | H | H | H | exo | " |
| 15 | — | —CO₂H | H | H | H | H | endo | " |
| 16 | = | —CO₂CH₃ | H | H | H | H | exo, endo | " |

| Example | A | B | $R^1$ | $R^2$ | $R^3$ | $R^4$ | config. | refernce |
|---|---|---|---|---|---|---|---|---|
| 17 | = | —C(=O)—CH₃ | H | H | H | H | endo | Synth. 1985, 798 |
| 18 | — | —CN | Cl | H | H | H | exo(CN) | " |
| 19 | — | —OH | H | H | H | H | endo[1] | EP-A 0,158,144 |
| 20 | — | —OH | H | H | H | H | exo[2] | " |
| 21 | — | —CH₂OH | H | H | H | H | endo | " |
| 22 | — | B + $R^1$ = 0 | | H | H | H | — | " |

[1] MP = 120° C.,
[2] Oil

EXAMPLE 23: TABLETS

Tablets suitable for oral administration and containing the ingredients specified hereinafter are prepared in a manner known per se by granulating the active substances and auxiliaries and then compressing the mixture to form tablets. These tablets are suitable for hypolipidemic treatment in a dose of one to two tablets 1–4 times a day.

| Ingredients (per tablet) | weight (mg) |
|---|---|
| Compound of Example 22 | 1 mg |
| Lactose | 50 mg |
| Corn starch | 15 mg |
| Talc | 1.5 mg |
| Colloidal silica | 1.5 mg |
| Magnesium stearate | 1 mg |

EXAMPLE 24: CAPSULES

Capsules suitable for oral administration contain the ingredients specified hereinafter and can be prepared in a manner known per se by mixing the active substances and auxiliaries and dispensing the mixture into gelatin capsules. These capsules are used for hypolipidemic treatment in a dose of one to two capsules 1–4 times a day.

| Ingredients (per capsule) | weight (mg) |
|---|---|
| Compound of Example 22 | 0.5 mg |
| Lactose | 50 mg |
| Corn starch | 15 mg |
| Talc | 1.5 mg |
| Colloidal silica | 1.5 mg |
| Magnesium stearate | 1 mg |

We claim:
1. A 7-diphenylmethylenebicycloheptane or 7-diphenylmethylenebicycloheptene of the formula Ia

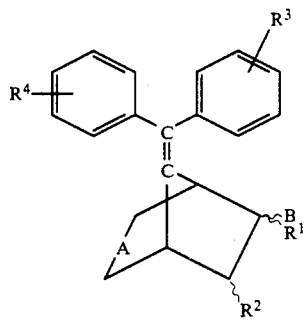

in which

A is a single or double bond;

B is a methyleneamino group of the formula

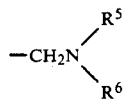

in which $R^5$ and $R^6$ are identical or different and denote hydrogen or $(C_1-C_4)$-alkyl, or in which $R^5$ and $R^6$ form, together with the nitrogen atom, a morpholine or piperazine ring, or a piperazine ring which is substituted in the 4-position by $(C_1-C_4)$-alkyl;

$R^1$ is hydrogen or chlorine;

$R^2$ is hydrogen; and $R^3$ and $R^4$ are identical or different and denote hydrogen, halogen, $(C_1-C_4)$-alkyl, $(C_1-C_4)$-alkoxy, trifluoromethyl, hydroxyl, amino, $(C_1-C_4)$-alkylamino or di-$(C_1-C_4)$-alkylamino; or a physiologically acceptable salt thereof.

2. A pharmaceutical composition for the treatment of hyperlipidemia, which comprises an effective amount for said treatment of a 7-diphenylmethylene-bicycloheptane or -heptene as claimed in claim 1 or physiologically acceptable salt thereof, together with a pharmaceutically acceptable carrier.

3. A method of treating hyperlipidemia, comprising the step of administering to a host in need of such treatment an effective amount of a 7-diphenylmethylenebicycloheptane or 7-diphenylmethylenebicycloheptene as claimed in claim 1, or a physiologically acceptable salt thereof.

4. A 7-diphenylmethylenebicycloheptane or 7-diphenylmethylene-bicycloheptene of the formula I

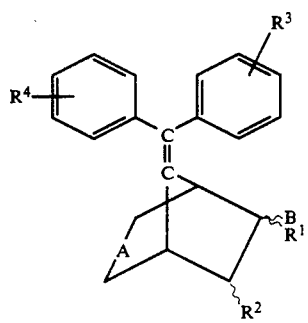

in which

A is a single or double bond;

B is a carboxamide group of the formula

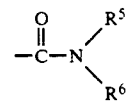

or a methyleneamino group of the formula

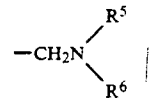

in which $R^5$ and $R^6$ are identical or different and denote hydrogen or $(C_1-C_4)$-alkyl, or in which $R^5$ and $R^6$ form, together with the nitrogen atom, a morpholine or piperazine ring, or a piperazine ring which is substituted in the 4-position by $(c_1-C_4)$-alkyl;

$R^1$ is hydrogen, chlorine or together with B, is an oxime group ($=$N—OH);

$R^2$ is hydrogen; and $R^3$ and $R^4$ are identical or different and denote hydrogen, halogen, $(C_1-C_4)$-alkyl, $(C_1-C_4)$-alkoxy, trifluoromethyl, hydroxyl, amino, $(C_1-C_4)$-alkoxy, trifluoromethyl, hydroxyl, amino, $(C_1-C_4)$-alkylamino or di-$(C_1-C_4)$-alkylamino; or a physiologically acceptable salt thereof.

5. A pharmaceutical composition for the treatment of hyperlipidemia, which comprises an effective amount for said treatment of a 7-diphenylmethylene-bicycloheptane or -heptene as claimed in claim 4, or physiologically acceptable salt thereof, together with a pharmaceutically acceptable carrier.

6. A method of treating hyperlipidemia, comprising the step of administering to a host in need of such treatment an effective amount of a 7-diphenylmethylenebicycloheptane or 7-diphenylmethylenebicycloheptene as claimed in claim 4, or a physiologically acceptable salt thereof.

7. A method of treating hyperlipidemia, comprising the step of administering to a host in need of such treatment an effective amount of a pharmaceutical composition comprising (a) an effective amount for said treatment of a 7-diphenylmethylenebicycloheptane or 7-diphenyl-methylenebicycloheptene of the formula I

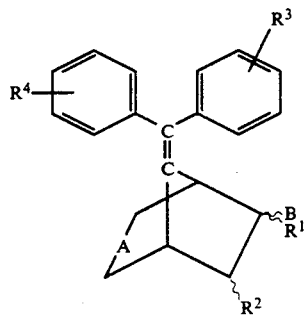

in which

A is a single or double bond;

B is a carboxamide group of the formula

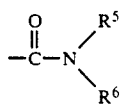

or a methyleneamino group of the formula

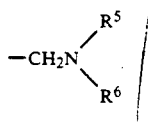

in which $R^5$ and $R^6$ are identical or different and denote hydrogen or $(C_1-C_4)$-alkyl, or in which $R^5$ and $R^6$ form, together with the nitrogen atom, a morpholine or piperazine ring, or a piperazine ring which is substituted in the 4-position by $(C_1-C_4)$-alkyl; or B is a —OH, —CN, —$CO_2H$, —$CO_2$-$(C_1-C_4)$-alkyl,

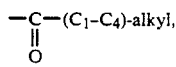

or $CH_2OH$ group;

$R^1$ is hydrogen, chlorine, $C_1-C_4$-alkyl or, together with B, an oxime group (=N—OH) or oxygen bonded by a double bond (=O);

$R^2$ is hydrogen or, together with B, is a dicarboxylic anhydride

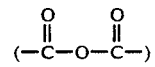

or a dicarboximide

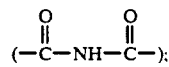

and $R^3$ and $R^4$ are identical or different and denote hydrogen, halogen, $(C_1-C_4)$-alkyl, $(C_1-C_4)$-alkoxy, trifluoromethyl, hydroxyl, amino, $(C_1-C_4)$-alkylamino or di-$(C_1-C_4)$-alkylamino; or a pharmaceutically acceptable salt thereof; together with (b) a pharmaceutically acceptable carrier.

* * * * *